(12) United States Patent
Bernardon

(10) Patent No.: US 7,700,657 B2
(45) Date of Patent: *Apr. 20, 2010

(54) VITAMIN D ANALOGS

(75) Inventor: Jean-Michel Bernardon, Nice (FR)

(73) Assignee: Galderma Research & Development, Biot (FR)

( * ) Notice: Subject to any disclaimer, the term of this patent is extended or adjusted under 35 U.S.C. 154(b) by 1809 days.

This patent is subject to a terminal disclaimer.

(21) Appl. No.: 10/718,538

(22) Filed: Nov. 24, 2003

(65) Prior Publication Data

US 2004/0224929 A1 Nov. 11, 2004

Related U.S. Application Data

(63) Continuation of application No. PCT/FR02/01726, filed on May 22, 2002.

(30) Foreign Application Priority Data

May 22, 2001 (FR) .................................. 01 06731

(51) Int. Cl.
*C07C 33/38* (2006.01)
*C07C 401/00* (2006.01)
*A61K 31/59* (2006.01)

(52) U.S. Cl. ..................... 514/649; 568/807; 568/644; 568/646; 568/631; 568/744; 568/645; 568/811; 564/373; 514/712; 514/713; 514/720; 514/728; 514/733; 514/736; 514/738

(58) Field of Classification Search ................ 552/653; 514/167, 649, 712, 713, 720, 728, 733, 736, 514/738; 560/73; 564/373; 568/646, 645, 568/644, 811, 631, 744, 807

See application file for complete search history.

(56) References Cited

U.S. PATENT DOCUMENTS 5,650,420 A 7/1997 Hall et al.

(Continued)

FOREIGN PATENT DOCUMENTS

EP 0 776 881 A1 6/1997
EP 0 850 909 A1 7/1998
WO WO 00/26167 5/2000

OTHER PUBLICATIONS

Bayuk et al., "The effects of pramipexole on cue induced craving" 38th Annual Meeting of American College of Neuropsychopharmacology, Abstract 51 (Dec. 1999).

(Continued)

*Primary Examiner*—Sabiha Qazi
(74) *Attorney, Agent, or Firm*—Buchanan Ingersoll & Rooney PC

(57) ABSTRACT

Novel vitamin D analogs, markedly active in the fields of cell proliferation and differentiation, are selected from among (4E,6E)-7-{3-[2-(3,4-bis-hydroxymethylphenyl)-ethyl]phenyl}-3-ethylnona-4,6-dien-3-ol, (E)-6-[3-(3,4-bis-hydroxymethylbenzyloxy)phenyl]1,1,1-trifluoro-2-trifluoromethyloct-5-en-3-yn-2-ol, (3E,5E)-6-[3-(3,4-bis-hydroxymethylbenzyloxy)-phenyl]-1,1,1-trifluoro-2-trifluoromethylocta-3,5-dien-2-ol, (E)-6-{3-[2-(3,4-bis-hydroxymethylphenyl)ethyl]phenyl}-1,1,1-trifluoro-2-trifluoromethyloct-5-en-3-yn-2-ol, and (3E,5E)-6-{3-[2-(3,4-bis-hydroxymethylphenyl)-ethyl]phenyl-1,1,1-trifluoro-2-trifluoromethylocta-3,5-dien-2-ol, and the geometric isomers thereof and these compounds in which one or more of the hydroxyl functions are protected by a protective group —(C=O)—R, in which R is a linear or branched alkyl radical having from 1 to 6 carbon atoms, an aryl radical having from 6 to 10 carbon atoms, or an aralkyl radical having from 7 to 11 carbon atoms, the aryl radical or the aralkyl radical optionally being mono- or disubstituted by a hydroxy group, an alkoxy radical having from 1 to 3 carbon atoms, a halogen atom, a nitro function or by an amino function, and mixtures thereof.

10 Claims, 6 Drawing Sheets

EXAMPLE 1

U.S. PATENT DOCUMENTS

| 5,877,342 | A  | 3/1999  | Bernardon et al. |
| 6,214,878 | B1 | 4/2001  | Bernardon et al. |
| 6,659,922 | B1 | 12/2003 | Yu |

OTHER PUBLICATIONS

Buydens-Branchey et al. "Buspirone attenuates withdrawal symptoms in cocaine addicts" *38th Annual Meeting of American College of Neuropsychopharmacology*, Abstract 52 (Dec. 1999).

Caine et al., "$D_3$ receptor test in vitro predicts decreased cocaine self-adminstration in rats" *NeuroReport* 8:2373-2377 (1997).

Eller et al., "Double-blind comparison of bromocriptine and placebo in cocaine withdrawal" *Am. J. Drug Alcohol Abuse* 21:65-79 (1995).

Filip et al., "The role of dopamine receptor subtypes in the discriminative stimulus effects of amphetamine and cocaine in rats" *Pol. J. Pharamcol.* 49:21-30 (1997).

Abstract of EP 417,637 A2, Kutter et al., Mar. 20, 1991.

Kang et al., "The Retinoid X Receptor Agonist 9-*cis*-Retinoic Acid and the 24-Hydroxylase Inhibitor Ketoconazole Increase Activity of 1,25-Dihydroxyvitamin $D_3$ in Human Skin In Vivo", The Journal of Investigative Dermatology, pp. 513-515, The Society for Investigative Dermatology, Inc., 1997.

International Search Report for PCT/FR02/01726.

EXAMPLE 1

EXAMPLE 59 OF D1

EXAMPLE 2

EXAMPLE 80 OF D1

EXAMPLE 3

EXAMPLE 92 OF D1

EXAMPLE 4

EXAMPLE 80 OF D1

EXAMPLE 5

EXAMPLE 60 OF D1

VITAMIN D ANALOGS

CROSS-REFERENCE TO PRIORITY/PCT APPLICATIONS

This application claims priority under 35 U.S.C. §119 of FR-01/06731, filed May 22, 2001, and is a continuation of PCT/FR 02/01726, filed May 22, 2002 and designating the United States (published in the French language on Nov. 28, 2002 as WO 02/094754 A1; the title and abstract were also published in English), both hereby expressly incorporated by reference.

BACKGROUND OF THE INVENTION

1. Technical Field of the Invention

The invention relates, by way of novel and useful industrial products, to biaromatic compounds which are vitamin D analogs.

The invention likewise relates to the process for their preparation and their utilization in pharmaceutical compositions intended for use in human or veterinary medicine, or else furthermore in cosmetic compositions.

The compounds according to the invention have a marked activity in the fields of cell proliferation and differentiation and are administered more particularly for the topical and systemic treatment of dermatological complaints, conditions or afflictions (or others) linked to a keratinization disorder, complaints, conditions or afflictions having an inflammatory and/or immunoallergic component and of hyperproliferation of tissues of ectodermal origin (skin, epithelium . . . ), whether benign or malignant. These compounds can in addition be used to combat aging of the skin, whether photoinduced or chronological and to treat cicatrization disorders.

It is likewise possible to use the compounds according to the invention in cosmetic compositions for body and hair hygiene.

2. Description of Background/Related/Prior Art

Vitamin D is a vitamin essential for the prevention and treatment of defects of cartilage mineralization (rachitis) and of bone (osteomalacia), and even of certain forms of osteoporosis in elderly subjects. However, it is now known that its functions extend even beyond the regulation of bone metabolism and of calcium homeostasis. Among these can be mentioned its actions on proliferation and on cell differentiation and the control of immune defenses. Their discovery has opened the way to novel therapeutic approaches in dermatology, cancerology, as well as in the field of autoimmune illnesses and that of organ or tissue transplantation.

An efficacious therapeutic contribution has long been known against the toxicity of this vitamin (sometimes fatal hypercalcemia). Currently, structural analogs of vitamin D are being synthesized, some of which only retain the differentiating properties and do not have any action on the calcium metabolism.

The assignee hereof has already proposed in WO 00/26167 (D1) novel compounds which are vitamin D analogs which show a selective activity on cell proliferation and differentiation without having hypercalcemic character. These compounds which are vitamin D analogs are in particular more easily synthesizable and therefore more economic with respect to what was known previously.

SUMMARY OF THE INVENTION

It has now surprisingly and unexpectedly been determined that certain compounds not specifically described in WO 00/26167 (D1) but confirming the general formula described elicit a biological activity very superior to that of the compounds specifically described. This activity is so strong that it approaches the activity of natural vitamin D.

Thus, the present invention relates to at least one compound selected from among the following compounds:

(4E,6E)-7-{3-[2-(3,4-bis-hydroxymethylphenyl)-ethyl]phenyl}-3-ethylnona-4,6-dien-3-ol;

(E)-6-[3-(3,4-bis-hydroxymethylbenzyloxy)phenyl]-1,1,1-trifluoro-2-trifluoromethyloct-5-en-3-yn-2-ol;

(3E,5E)-6-[3-(3,4-bis-hydroxymethylbenzyloxy)-phenyl]-1,1,1-trifluoro-2-trifluoromethylocta-3,5-dien-2-ol;

(E)-6-{3-[2-(3,4-bis-hydroxymethylphenyl)ethyl]-phenyl}-1,1,1-trifluoro-2-trifluoromethyloct-5-en-3-yn-2-ol;

(3E,5E)-6-{3-[2-(3,4-bis-hydroxymethylphenyl)-ethyl]phenyl-1,1,1-trifluoro-2-trifluoromethylocta-3,5-dien-2-ol, as well as their geometric isomers and these compounds in which one or more of the hydroxyl functions are protected by a protective group of type —(C=O)—R, with R representing a linear or branched alkyl radical having from 1 to 6 carbon atoms, or an aryl radical having from 6 to 10 carbon atoms, or an aralkyl radical having from 7 to 11 carbon atoms, the aryl radical or the aralkyl radical being able to be mono- or disubstituted by a hydroxy group, by an alkoxy group having from 1 to 3 carbon atoms, by a halogen atom, by a nitro function or by an amino function, and their mixtures.

Linear or branched alkyl radical having from 1 to 6 carbon atoms is understood as preferably meaning a methyl, ethyl, isopropyl, tert-butyl or hexyl radical.

Aryl radical having from 6 to 10 carbon atoms is understood as meaning a phenyl or naphthyl radical.

Aralkyl radical having from 7 to 11 carbon atoms is understood as meaning a benzyl or methylnaphthyl radical.

Halogen atom is understood as meaning a fluorine, bromine or chlorine atom.

The present invention likewise relates to the processes for preparation of the compounds indicated above.

Figure 1:
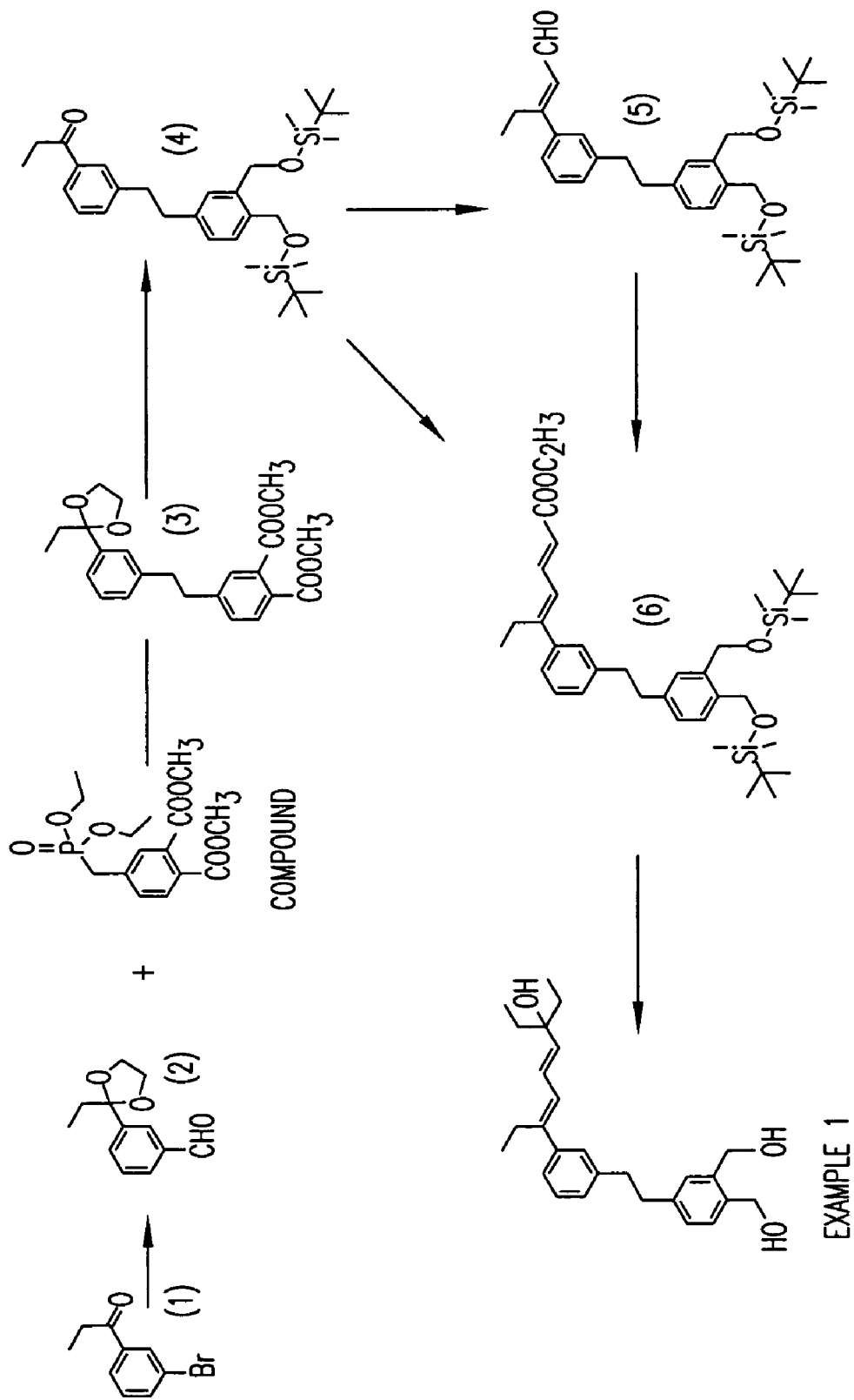
FIG. 1 is a diagram of a chemical pathway for the production of the compound of Example 1.
Figure 2:
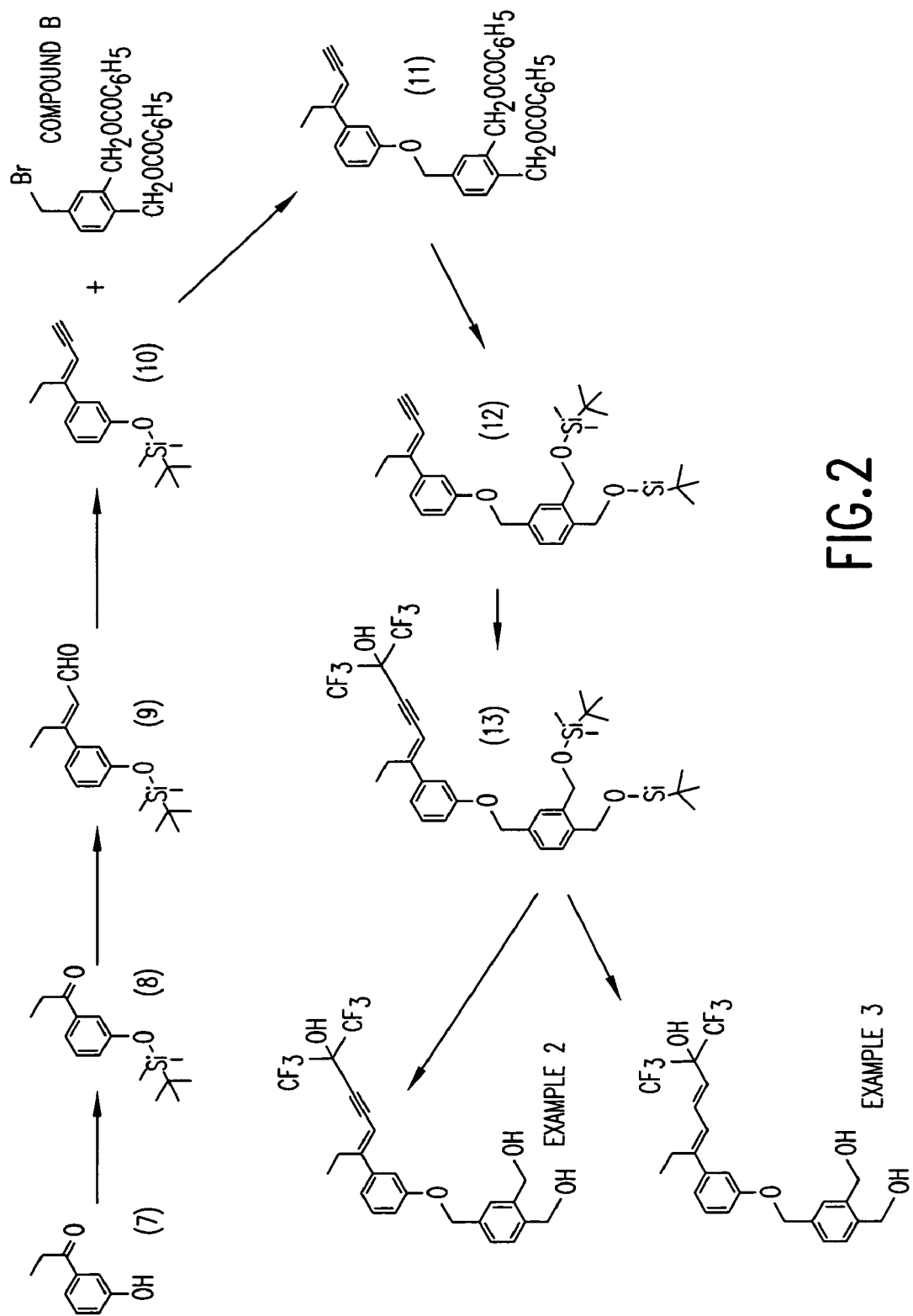
FIG. 2 is a diagram of a chemical pathway for the production of the compounds of Examples 2 and 3.
Figure 3:
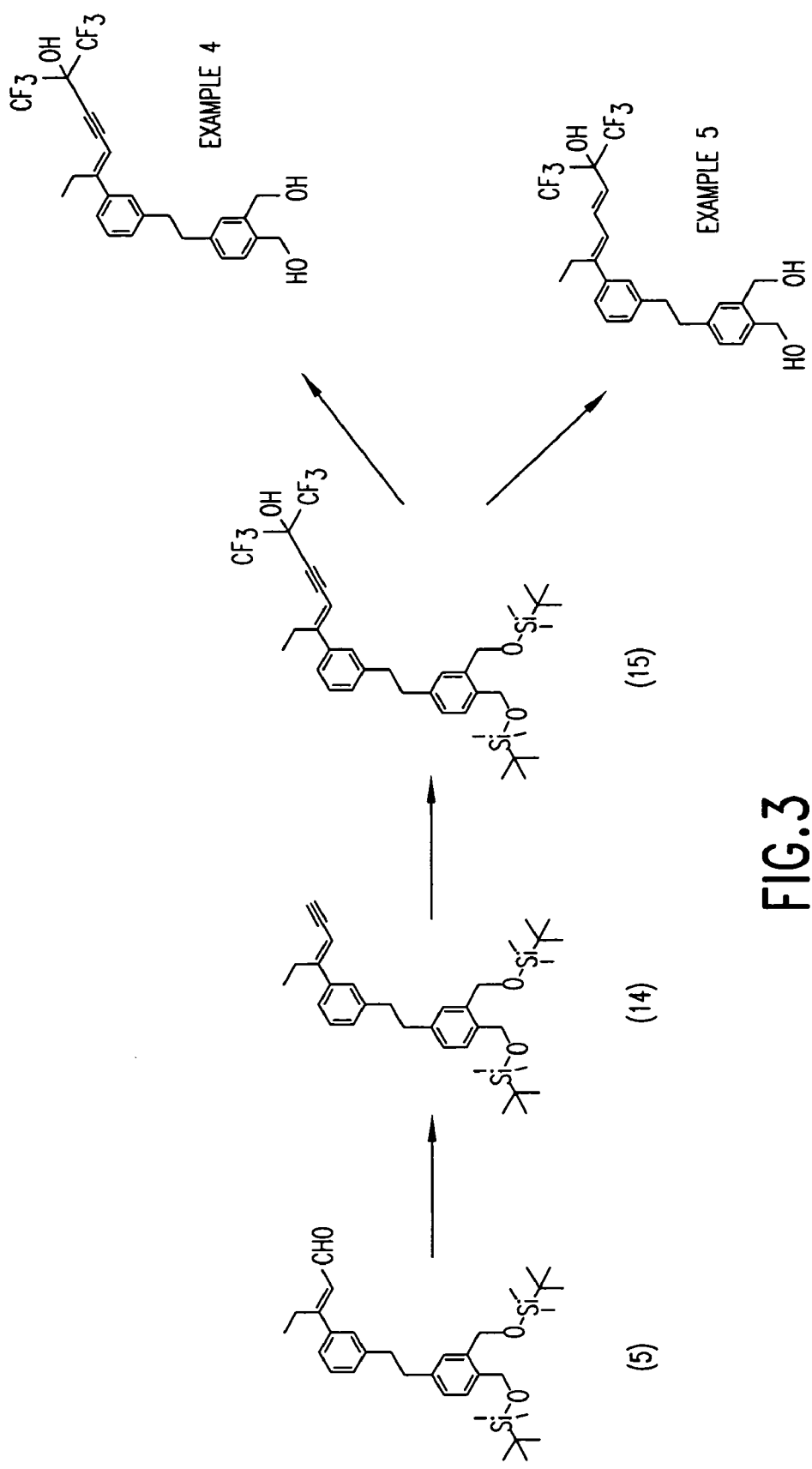
FIG. 3 is a diagram of a chemical pathway for the production of the compounds of Examples 4 and 5.

DETAILED DESCRIPTION OF BEST MODE AND SPECIFIC/PREFERRED EMBODIMENTS OF THE INVENTION

FIGS. 1 to 4 represent reaction schemes which can be employed for the preparation of the compounds according to the invention.

Thus, the compound of example 1 can be obtained (FIG. 1) starting from the derivative (6) by reaction with ethyllithium at −78° C. in a solvent such as THF and then deprotection of the hydroxyl groups in the presence of tetrabutylammonium fluoride.

The compound (6) can be obtained starting from 3-bromo-propiophenone (1) by a reaction sequence comprising:

the formation of the derivative (2) by protection of the ketone function in dioxolane form and then the formation of the aldehyde function starting from the corresponding lithien in the presence of DMF.

The formation of the derivative (3) by a reaction of the Horner-Emmons type between the phosphonate derivative (compound A) and the benzaldehyde (2), then hydrogenation in the presence of palladium on carbon.

The formation of the derivative (4) by reduction of the ester functions in the presence of lithium aluminum hydride, deprotection of the ketone in the presence of para-toluenesulfonic acid and protection of the alcohol functions in the form of tert-butyldimethylsilyl.

The formation of the derivative (5) by a reaction of Horner-Emmons type with triethyl phosphono-acetate and then reduction of the ester function in the presence of lithium aluminum hydride and oxidation of the alcohol function in the presence of manganese dioxide.

The formation of the derivative (6) by a reaction of Horner-Emmons type between triethyl phosphono-acetate and the aldehyde derivative (5) or directly by a reaction of Homer-Emmons type between triethyl phosphonocrotonate and the ketone derivative (4).

Figure 4:
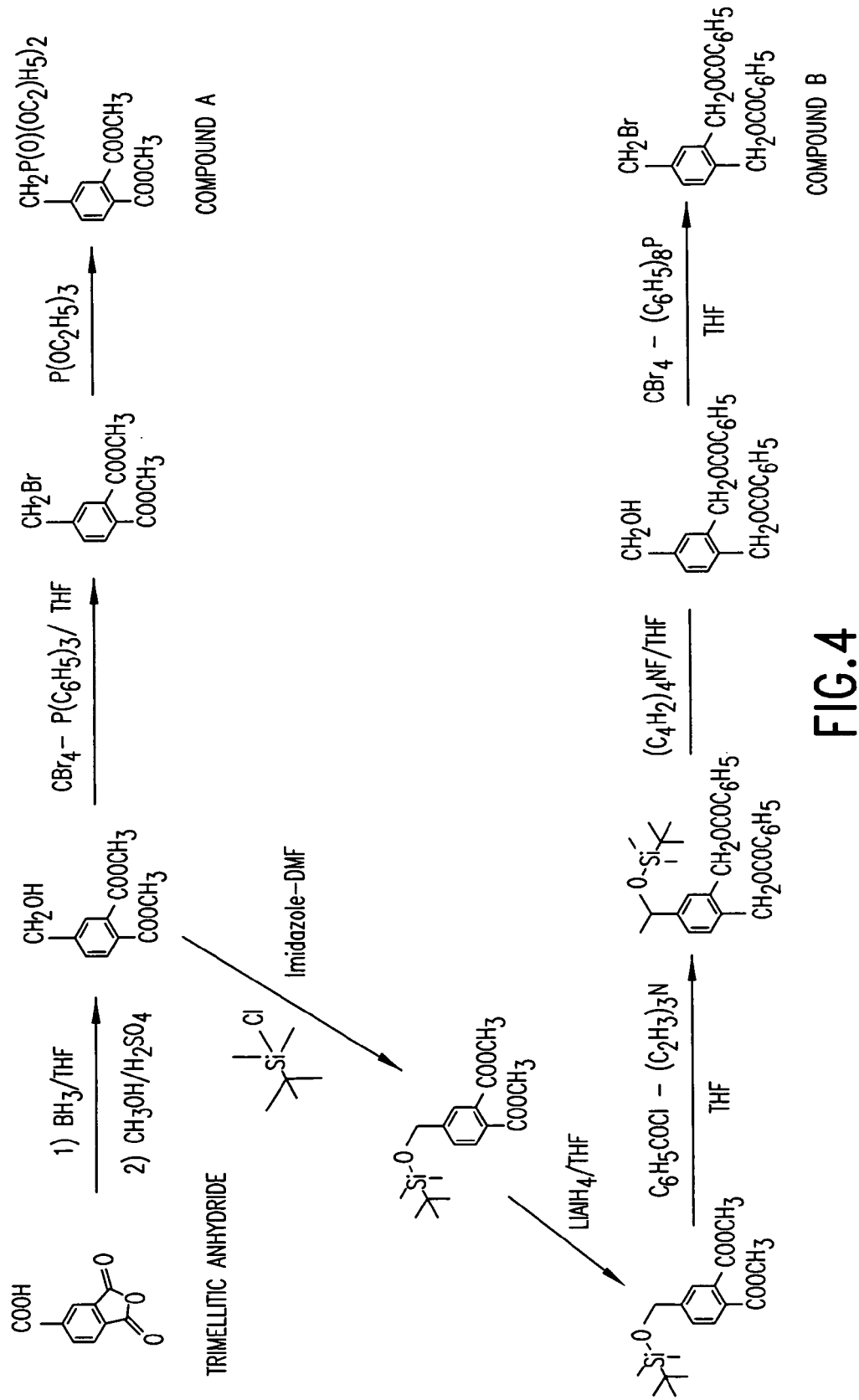
FIG. 4 is a diagram of a chemical pathway for the production of Compound A and Compound B.

The compound A being able to be prepared starting from trimellitic anhydride according to the reaction scheme represented in FIG. 4.

The compounds of examples 2 and 4 can be obtained (FIGS. 2 and 3) respectively starting from the derivative (13) and from the derivation (15) by deprotection of the alcohol functions in the presence of tetrabutylammonium fluoride.

The compounds of examples 3 and 5 can be obtained (FIGS. 2 and 3) respectively starting from the derivative (13) and from the derivation (15) by reduction of the triple bond to a double bond of trans configuration with lithium aluminum hydride in the presence of sodium methoxide in a solvent such as THF and then deprotection of the alcohol functions in the presence of tetrabutylammonium fluoride.

The compound (13) being able to be obtained starting from 3-hydroxypropiophenone (7) by a reaction sequence comprising:

The formation of the derivative (8) by protection of the phenol group in the form of tert-butyl-dimethylsilyl.

The formation of the derivative (9) by a reaction of Homer-Emmons type with triethyl phosphono-acetate and then reduction of the ester function in the presence of lithium aluminum hydride and oxidation of the alcohol function in the presence of manganese dioxide.

The formation of the derivative (10) by a reaction of Corey-Fuchs type.

The formation of the derivative (11) by deprotection of the phenolic function and then coupling reaction with the brominated derivative (compound B) in the presence of sodium hydride in a solvent such as DMF.

The formation of the derivative (12) by deprotection of the benzoate groups and then reprotection in the form of tert-butyldimethyl-silyloxy groups.

The formation of the derivative (13) by reaction with butyl-lithium and then with hexafluoroacetone.

The compound B being able to be prepared starting from trimellitic anhydride according to the reaction scheme represented in FIG. 4.

The compound (15) being able to be obtained starting from the derivative (5) by transformation of the aldehyde function to an acetylenic function (14) according to a reaction of Corey-Fuchs type and then lithiation with butyllithium and reaction with hexa-fluoroacetone.

The protection of the hydroxy functions takes place by a customary method as described in the literature, for example by reaction of a corresponding acid chloride of type RCOCl in a solvent such as THF or dichloromethane in the presence of a base such as pyridine or triethylamine.

The compounds according to the invention have biological properties analogous to those of vitamin D, especially the properties of transactivation of vitamin D response elements (VDRE), such as an agonist activity with respect to receptors of vitamin D or of its derivatives. Vitamins D or their derivatives are understood as meaning, for example, the derivatives of vitamin D2 or D3 and in particular 1,25-dihydroxy-vitamin D3 (calcitriol).

This agonist activity with respect to vitamin D receptors or its derivatives can be demonstrated "in vitro" by methods recognized in the field of the study of gene transcription (Hansen et al., The Society For Investigative Dermatologie, vol. 1, No 1, April 1996).

By way of example, the VDR agonist activity can be tested on the HeLa cell line by cotransfection of an expression vector for the human VDR receptor and of the reporter plasmid p240Hase-CAT. The agonist activity can be characterized in this cotransfection system by the determination of the dose necessary to obtain 50% of the maximum activity of the product (AC50). The detail of the protocol of this test as well as the results obtained with the compounds according to the invention are described in example 7 of the present application.

The biological properties analogous to vitamin D can likewise be measured by the capacity of the product to inhibit the proliferation of normal human keratinocytes (NHK in culture). The product is added to NHK cultured under conditions favoring the proliferative state. The product is left in contact with the cells for five days. The number of proliferative cells is measured by incorporation of bromodeoxyuridine (BRdU) into the DNA. The protocol of this test as well as the results obtained with the compounds according to the invention are described in example 8 of the present application.

The biological properties analogous to vitamin D can likewise be measured by the capacity of the product to induce the differentiation of HL60 promyelocytic leukemia cells. The protocol of this test as well as the results obtained with the compounds according to the invention are described in example 9 of the present application.

The agonist activity on vitamin D receptors of the compounds of the invention can be likewise evaluated "in vivo" by induction of 24-hydroxylase in SKH mice. (Kang et. al., Journal of Investigative Dermatology, 1997, 108(4), 513-518). The test protocol used as well as the results obtained with the compounds according to the invention are described in example 10 of the present application. 1]:

The present invention likewise relates by way of medicament to the compounds described above.

The compounds according to the invention are particularly highly suitable in the following fields of treatment:

dermatological complaints linked to a keratinization disorder having a bearing on differentiation and proliferation such as common acne, blackheads, polymorphs, rosacea, nodulocystic acne, acne conglobata, senile acne, secondary acne such as solar, medicinal or professional acne;

ichthyosis, ichthyosiform states, Damier's syndrome, palmoplantar keratodermia, leucoplasia and leucoplasiform states, cutaneous or mucous (buccal) lichen;

dermatological complaints with an inflammatory immunoallergic component, with or without cell proliferation disorder, and such as all forms of psoriasis, whether it be cutaneous, mucous or ungual, and even psoriatic rheumatism, or else cutaneous atopy, such as eczema or respiratory atopy or else gingival hypertrophy;

dermal or epidermal proliferations whether they are benign or malignant, whether they are or are not of viral origin such as common warts, planar warts and verruciform epidermodysplasia, oral or florid papillomatoses, T lymphoma, and proliferations being able to be induced by ultraviolet, especially in the case of baso- and spinocellular epithelioma, as well as cutaneous precancerous lesions such as keratoacanthomas;

immune dermatoses such as lupus erythematosus, bullous immune diseases or collagen diseases, such as scleroderma;

dermatological or general complaints with an immunological component;

sebaceous function disorders such as hyper-seborrhea of acne or simple seborrhea;

cutaneous disorders due to exposure to UV rays, aging of the skin, whether it be photoinduced or chronological, pigmentations and actinic keratoses, or any pathologies associated with chronological or actinic aging;

cicatrization disorders or stretch marks, inflammatory complaints such as arthritis, complaints of viral origin at the cutaneous or general level, such as Kaposi's syndrome;

ophthalmological complaints, especially corneopathy;

cancerous or precancerous states of cancers having or being able to be induced by vitamin D receptors, such as breast cancer, leukemia, myelodysplasic syndromes and lymphomas, carcinomas of the cells of the malpighian epithelium and gastrointestinal cancers, melanomas, and osteosarcoma;

alopecia of different origins, especially alopecia due to chemotherapy or to radiation;

immune complaints, such as autoimmune diseases, diabetes mellitus of type 1, multiple sclerosis, lupus and lupus type complaints, asthma, glomerulonephritis; selective dysfunctions of the immune system, such as AIDS, immune rejection;

endocrine complaints;

complaints characterized by an abnormal management of intracellular calcium, pathologies in which the calcium metabolism is involved, such as muscular ischemia;

deficiencies in vitamin D and other complaints of the homeostasis of minerals in the plasma and the bones, such as rachitis, osteomalacia, osteoporosis, especially in the case of menopausal women, renal osteodystrophia, or complaints of the parathyroid function;

complaints of the cardiovascular system such as arteriosclerosis or hypertension as well as non-insulin-dependent diabetes.

In the therapeutic fields mentioned above, the compounds according to the invention can be advantageously employed in combination with retinoids, with corticosteroids or estrogens, in association with antioxidants, with $\alpha$-hydroxy acids, $\beta$-hydroxy acids or $\alpha$-keto acids or their derivatives, with ion channel blockers, or else in association with other medicaments known to interfere with the immune system (for example cyclosporin, FK 506, glucocorticoids, monoclonal antibodies, cytokines or growth factors . . . ).

Retinoids are understood as meaning natural or synthetic ligands of the RAR or RXR receptors.

Antioxidants are understood as meaning, for example, $\alpha$-tocopherol, superoxide dismutase, ubiquinol or certain metal chelators.

$\alpha$-Hydroxy or $\alpha$-keto acids or their derivatives are understood as meaning, for example, lactic, malic, citric, glycolic, mandelic, tartaric, glyceric, ascorbic acids, as well as their salts, amides or esters.

$\beta$-Hydroxy acids or their derivatives are understood as meaning, for example, salicylic acid as well as its salts, amides or esters.

Ion channel blockers are understood as meaning, for example, potassium channel blockers, and in particular minoxidil (2,4-diamino-6-piperidino-pyrimidine 3-oxide) and its derivatives.

The present invention likewise relates to a pharmaceutical composition comprising at least one compound such as defined above.

The administration of the compounds according to the invention can be carried out by the enteral, parenteral, topical or ocular route.

By the enteral route, the pharmaceutical compositions can be present in the form of tablets, of gelatine capsules, of coated tablets, of syrups, of suspensions, of solutions, of powders, of granules, of emulsions, of microspheres or nanospheres or lipid vesicles or polymers allowing controlled release. By the parenteral route, the compositions can be present in the form of solutions or suspensions for perfusion or for injection. The compounds according to the invention are generally administered in a daily dose of approximately 0.001 µg/kg to 1,000 µg/kg and preferably of approximately 0.01 µg/kg to 100 µg/kg of body weight in 1 to 3 doses.

By the topical route, the pharmaceutical compositions based on compounds according to the invention are intended for the treatment of the skin and of the mucous membranes and are present in the form of salves, of creams, of milks, of ointments, of powders, of moistened swabs, of solutions, of gels, of sprays, of lotions or of suspensions. They can likewise be present in the form of microspheres or nanospheres or lipid or polymeric vesicles or polymeric patches and of hydrogels allowing controlled release. These compositions by the topical route can be present either in anhydrous form, or in aqueous form according to the clinical indication.

By the ocular route, these are principally eye lotions.

These compositions for the topical or ocular route contain at least one compound according to the invention in a concentration of preferably between 0.0001 and 5% and preferably between 0.001% to 1% with respect to the total weight of the composition.

The compounds according to the invention are likewise used in the cosmetic field, in particular in bodily and hair hygiene and especially for the treatment of skin with a tendency to acne, for the regrowth of the hair, prevention of hair loss, to combat the greasy aspect of the skin or of the hair, in protection against the harmful effects of the sun or in the treatment of physiologically dry skin, in order to prevent and/or to combat photoinduced or chronological aging.

In the cosmetic field, the compounds according to the invention can be advantageously employed in combination with the retinoids, with corticosteroids, in association with antioxidants, with $\alpha$-hydroxy or $\alpha$-keto acids or their derivatives, or else with ion channel blockers.

The different products combined with the compounds of the present invention are such as defined above.

The present invention therefore likewise aims at a cosmetic composition containing, in a cosmetically acceptable support, at least one compound such as defined above. This cosmetic composition can be present especially in the form of a cream, of a milk, of a lotion, of a gel, of microspheres or nanospheres or lipid or polymeric vesicles, of a soap or of a shampoo.

The concentration of compound according to the invention in the cosmetic compositions can be between 0.001% and 3% by weight with respect to the total weight of the composition.

The pharmaceutical and cosmetic compositions according to the invention can, in addition, contain inert or even pharmacodynamically or cosmetically active additives or combinations of these additives and especially: wetting agents; depigmenting agents such as hydroquinone, azelaic acid, caffeic acid or kojic acid; emollients; hydrating agents such as glycerol, PEG 400, thiamorpholinone and its derivatives or urea; antiseborrheic or antiacne agents, such as S-carboxymethylcysteine, S-benzylcysteamine, their salts and their derivatives, or benzoyl peroxide; antibiotics such as erythromycin and its esters, neomycin, clindamycin and its esters, the tetracyclines; antifungal agents such as ketoconazole or the polymethylene-4,5-isothiazolin-3-ones; agents favoring the regrowth of the hair, such as minoxidil (2,4-di-amino-6-piperidinopyrimidine 3-oxide) and its derivatives, diazoxide (7-chloro-3-methyl-1,2,4-benzo-thiadiazine 1,1-dioxide) and phenytoin (5,4-diphenyl-imidazolidine-2,4-dione); non-steroidal anti-inflammatory agents; carotenoids and, especially, β-carotene; antipsoriatic agents such as anthralin and its derivatives and finally eicosa-5,8,11,14-tetra-ynoic and eicosa-5,8,11-trynoic acids, their esters and amides.

The compositions according to the invention can likewise contain agents for improving the taste, preservatives such as esters of parahydroxybenzoic acid, stabilizers, humidity regulators, pH regulators, osmotic pressure modifiers, emulsifiers, UV-A and UV-B filters, antioxidants, such as α-tocopherol, butylhydroxyanisole or butylhydroxytoluene.

In order to further illustrate the present invention and the advantages-thereof, the following specific examples are given, it being understood that same are intended only as illustrative and in nowise limitative. The examples to follow also present various actual formulations based on such compounds as well as examples of the evaluation test of the biological activity of the compounds according to the invention.

Example 1

(4E,6E)-7-{3-[2-(3,4-Bis-hydroxymethylphenyl) ethyl]-phenyl}-3-ethylnona-4,6-dien-3-ol (a) 2-(3-Bromophenyl)-2-ethyl[1,3]dioxolane 15 g (70 mmol) of 3-bromopropiophenone are dissolved in 250 ml of toluene, and 20 ml (350 mmol) of ethylene glycol are added, as well as 660 mg (3.5 mmol) of paratoluenesulfonic acid. The assembly is equipped with a Dean-Stark type water extractor, and the reaction medium and raised to reflux for 20 h. After cooling, treatment with a solution of potassium bicarbonate and extraction with ethyl ether, the desired product is pure without purification, and obtained in the form of yellowish oil (m=17.8 g; Y=99%).

(b) 3-(2-Ethyl[1,3]dioxolan-2-yl)benzaldehyde 17.8 g (70 mmol) of 2-(3-bromophenyl)-2-ethyl-[1,3]dioxolane are dissolved in 300 ml of THF and the mixture is cooled to −78° C. 34 ml (85 mmol) of a 2.5 M solution of butyllithium are added slowly, and the mixture is stirred for 30 minutes. 8.1 ml (105 mmol) of DMF are then added, and the mixture is brought back to 0° C., then treated with a saturated solution of ammonium chloride. After extraction with ethyl ether, the desired aldehyde is obtained in the form of yellow oil (m=14 g; Y=97%).

(c) Dimethyl 4-{(E)-2-[3-(2-ethyl[1,3]dioxolan-2-yl)-phenyl]vinyl}phthalate 10.3 g (30 mmol) of dimethyl 4-(diethoxy-phosphorylmethyl) phthalate are dissolved in 100 ml of anhydrous THF, and the mixture is cooled to 0° C. 3.4 g (30 mmol) of potassium tert-butoxide are added in portions, and the mixture is stirred for 30 minutes. A solution of 5.6 g (27.3 mmol) of 3-(2-ethyl-[1,3]dioxolan-2-yl)benzaldehyde in 50 ml of THF is then added drop by drop, and the medium is stirred for 2 hours at 0° C. After the usual treatment, the residue is purified by chromatography on a silica column (eluent heptane 80—ethyl acetate 20). A yellow oil is obtained (m=9.6 g; Y=89%).

(d) Dimethyl 4-{2-[3-(2-ethyl[1,3]dioxolan-2-yl)-phenyl]ethyl}phthalate 9.5 g (24 mmol) of dimethyl 4-{(E)-2-[3-(2-ethyl-[1,3]dioxolan-2-yl)-phenyl]ethyl}phthalate are dissolved in a mixture of 120 ml of ethyl acetate and 5 ml of triethylamine. The reaction mixture is degassed with a flow of nitrogen for 10 minutes, then 1 g of 5% palladium on carbon is added. The reaction medium is then heated to 80° C. while a pressure of 4 bar of hydrogen is applied for 4 hours. The medium is then filtered and concentrated under reduced pressure. The residue is purified by chromatography on a silica column. A colorless oil is obtained (m=7.5 g; Y=80%).

(e) (4-{2-[3-(2-Ethyl[1,3]dioxolan-2-yl)phenyl]ethyl}-2-hydroxymethylphenyl)methanol 2.9 g (75 mmol) of lithium aluminum hydride are suspended in 20 ml of ethyl ether. A solution of 7.5 g (19 mmol) of dimethyl 4-{2-[3-(2-ethyl[1,3]dioxolan-2-yl)phenyl] ethyl}phthalate in 100 ml of ethyl ether is added drop by drop. After stirring at ambient temperature for 20 minutes, the reaction medium is treated by addition of 15 ml of water, 1.5 ml of 15% sodium carbonate and 4.5 ml of water, then filtered and concentrated under reduced pressure. A colorless oil is obtained (m=6.4 g; Y=99%).

(f) 1-{3-[2-(3,4-Bis-hydroxymethylphenyl)ethyl]-phenyl}propan-1-one 6.4 g (18.7 mmol) of (4-{2-[3-(2-ethyl-[1,3]dioxolan-2-yl) phenyl]ethyl}2-hydroxymethyl-phenyl)methanol are dissolved in a mixture of 40 ml of water and 40 ml of acetone. 650 mg of paratoluene-sulfonic acid are added, and the medium is stirred for 5 hours. After the usual treatment, the desired product is pure without purification, and obtained in the form of colorless oil (m=5.57 g; Y=100%).

(g) 1-(3-{2-[3,4-Bis(tert-butyldimethylsilanyloxymethyl)phenyl]ethyl}phenyl)propan-1-one 5.5 g (18.5 mmol) of 1-{3-[2-(3,4-bishydroxy-methylphenyl) ethyl]phenyl}propan-1-one are dissolved in 50 ml of anhydrous DMF, and the mixture is cooled to 0° C. 6.7 g (45 mmol) of tert-butyldimethylchlorosilane and 3.5 g (52 mmol) of imidazole are added. The medium is brought back to ambient temperature and is stirred for 2 h. After treatment with a saturated solution of ammonium chloride and then extraction with ethyl acetate, the organic phases are collected, rinsed with water, dried and concentrated under reduced pressure. A colorless oil is obtained (m=9.6 g; Y=99%).

(h) Ethyl (E)-3-(3-{2-[3,4-bis(tert-butyldimethyl-silanyloxymethyl)phenyl]ethyl}phenyl)pent-2-enoat 11.1 ml (56 mmol) of triethyl phosphono-acetate are dissolved in 100 ml of THF. 2.2 g (55 mmol) of 60% sodium hydride are then added, and the medium is stirred for 30 minutes at ambient temperature. A solution of 9.5 g (18 mmol) of 1-(3-{2-[3,4-bis(tert-butyldimethylsilanyloxymethyl) phenyl]ethyl}phenyl)-propan-1-one in 100 ml of THF is then added drop by drop. The medium is stirred for 6 hours, then treated with water and extracted with ethyl acetate. The residue obtained is purified by chromatography on silica gel (eluent ethyl acetate 10-heptane 90). A yellow oil is obtained (m=5.8 g; Y=56%).

(i) (E)-3-(3-{2-[3,4-Bis(tert-butyldimethylsilany-loxy-methyl)phenyl]ethyl}phenyl)pent-2-en-1-ol 0.75 g (19 mmol) of lithium aluminum hydride are suspended in 10 ml of ethyl ether. A solution of 5.6 g (9.6 mmol) of ethyl (E)-3-(3-{2-[3,4-bis(tert-butyldimethylsilany-loxmethly)phenyl]ethyl}phenyl)pent-2-enoate in 50 ml of ethyl ether is added drop by drop. After stirring at ambient temperature for 20 minutes, the reaction medium is treated by addition of 0.75 ml of water, 0.75 ml of 15% sodium carbonate and 1.5 ml of water, then filtered and concentrated under reduced pressure. A colorless oil is obtained (m=5.26 g; Y=99%).

(j) (E)-3-(3-{2-[3,4-Bis(tert-butyldimethylsilany-loxy-methyl)phenyl]ethyl}phenyl)pent-2-enal 2.8 g (5 mmol) of (E)-3-(3-{2-[3,4-bis(tert-butyldimethyl-silanyloxymethyl)phenyl]ethyl}phenyl)pent-2-en-1-ol are dissolved in 50 ml of dichloromethane. 4.3 g (50 mmol) of manganese dioxide are added, and the reaction medium is stirred for 12 hours, then filtered and concentrated under reduced pressure. The desired product is obtained in the form of yellow oil (m=2.8 g; Y=100%).

(k) Ethyl (2E,4E)-5-(3-{2-[3,4-bis(tert-butyldim-ethyl-silanyloxymethyl)phenyl]ethyl)phenyl)hepta-2,4-dienoate 1.3 ml (6.4 mmol) of triethyl phosphono-acetate are dissolved in 20 ml of THF. 260 mg (6.5 mmol) of 60% sodium hydride are then added, and the medium is stirred for 30 minutes at ambient temperature. A solution of 2.8 g (5 mmol) of (E)-3-(3-{2-[3,4-bis(tert-butyldimethylsilanyloxym-ethyl)-phenyl]ethyl}phenyl)pent-2-enal in 30 ml of THF is then added drop by drop. The medium is stirred for 6 hours, then treated with water and extracted with ethyl acetate. The residue obtained is purified by chromatography on silica gel (eluent ethyl acetate 10-heptane 90). A yellow oil is obtained (m=2.52 g; Y=81%).

(l) (4E,6E)-7-{3-[2-(3,4-Bis-hydroxymethylphenyl)-ethyl]phenyl}-3-ethylnona-4,6-dien-3-ol 1.7 g (2.7 mmol) of ethyl (2E,4E)-5-(3-{2-[3,4-bis(tert-butyldimethylsilanyloxymethyl)phenyl]-ethyl}phenyl) hepta-2,4-dienoate are dissolved in 120 ml of anhydrous THF, and the mixture is cooled to −78° C. 13.5 ml (13.5 mmol) of a solution of ethyllithium (1.0-1.5 M) are added, and the medium is stirred at this temperature for 1 hour, then brought back to 0° C. and treated with a saturated solution of ammonium chloride. The residue obtained is dissolved in 50 ml of THF and then 6.5 ml (6.5 mmol) of a solution of tetrabutylammonium fluoride is added. After stirring for 30 minutes and the usual treatment, the residue obtained is purified by chromatography on a silica column. The desired product is obtained in the form of colorless oil (m=200 mg; Y=18%).

$^1$H NMR (DMSO): 0.82 (t, 6H, J=7.5 Hz); 0.89 (t, 3H, J=7.4 Hz); 1.41-1.53 (m, 4H); 2.41 (q, 2H, J=7.4 Hz); 2.83 (s, 4H); 4.01 (s, 1H); 4.41 (t, 2H, J=8 Hz); 4.45 (t, 2H, J=8 Hz); 4.94-4.98 (m, 2H); 6.31 (d, 1H, J=15.0 Hz); 6.46 (d, 1H, J=11.0 Hz); 7.08-7.29 (m, 7H); 7.42-7.45 (m, 1H).

Example 2

(E)-6-[3-{3,4-Bis-hydroxymethylbenzyloxy)phenyl]-1,1,1-trifluoro-2-tifluoromethyloct-5-en-3-yn-2-ol

(a) 3-(tert-butyldimethylsilanyloxy)benzaldehyde

In a manner analogous to example 1 g, by reaction of 42.7 g (0.275 mol) of tert-butyldimethylchlorosilane with 30.5 g (0.2 mol) of 3-hydroxybenzaldehyde and (20.4 g, 0.3 mol) of imidazole. After purification on a silica column (dichloromethane 20-heptane 80), a yellow oil is obtained (m=55.9 g; Y=95%).

(b) 1-[3-(tert-Butyldimethylsilanyloxy)phenyl]pro-pan-1-ol 50 g (0.21 mol) of 3-(tert-butyldimethyl-silanyloxy)benzaldehyde are dissolved in 500 ml of ethyl ether and the mixture is cooled to 0° C. 80 ml (0.24 mol) of a 3.0 M solution of ethylmagnesium bromide are added slowly, and the mixture is stirred for 5 hours. After the usual treatment, the residue obtained is purified by chromatography on a silica column (eluent ethyl acetate 20/hexane 80). A colorless oil is obtained (m=45.8 g; Y=82%).

(c) 1-[3-(tert-Butyldimethylsilanyloxy)phenyl]pro-pan-1-one

In a manner analogous to example 1j, by reaction of 45 g (0.17 mol) of 1-[3-(tert-butyldimethylsilanyloxy)phenyl] propan-1-ol with (148 g, 1.7 mol) of manganese dioxide. A yellow oil is obtained (m=45 g, Y=100%).

(d) Ethyl (E)-3-[3-(tert-butyldimethylsilanyloxy)-phenyl]pent-2-enoate 22.5 ml (113 mmol) of triethyl phosphono-acetate are dissolved in 100 ml of THF. 4.5 g (113 mmol) of 60% sodium hydride are then added, and the medium is stirred for 30 minutes at ambient temperature. A solution of 20 g (75.6 mmol) of 3-(tert-butyldimethylsilanyloxy)propan-1-one in 100 ml of THF is then added drop by drop. The medium is stirred for 6 hours, then treated with water and extracted with ethyl acetate. The residue obtained is purified by chromatography on silica gel (eluent ethyl acetate 10-heptane 90). A yellow oil is obtained (m=7.6 g; Y=30%).

(e) (E)-3-[3-(tert-Butyldimethylsilanyloxy)phenyl] pent-2-en-1-ol

In a manner analogous to example 1e, by reaction of 7.6 g (23 mmol) of ethyl (E)-3-[3-(tert-butyldimethylsilanyloxy) phenyl]pent-2-enoate with 1.05 g (25 mmol) of lithium aluminum hydride. A colorless oil is obtained (m=6.7 g; Y=100%).

(f) (E)-3-[3-(tert-Butyldimethylsilanyloxy)phenyl] pent-2-en-1-al

In a manner analogous to example 1j, by reaction of 6.7 g (23 mmol) of (E)-3-[3-(tert-butyldimethylsilanyloxy)phenyl] pent-2-en-1-ol with 10 g (115 mmol) of manganese dioxide. A yellow oil is obtained (m=4.7 g; Y=71%).

(g) tert-Butyl-[3-((E)-4,4-dibromo-1-ethylbuta-1,3-dienyl)phenoxy]dimethylsilane 1.17 g (18 mmol) of zinc powder, 4.7 g (18 mmol) of triphenylphosphine and 5.9 g (18 mmol) of carbon tetrabromide are stirred for 45 minutes in 150 ml of dichloromethane. A solution of 2.6 g (9 mmol) of (E)-3-[3-(tert-butyldimethylsilanyloxy)phenyl]pent-2-en-1-al in 10 ml of dichloromethane is added drop by drop. The reaction medium is stirred for 1 hour, then extracted with a mixture of water and of dichloro-methane. The residue is filtered on a silica column (eluent dichloromethane). A yellow oil is obtained (m=3.3 g; Y=83%).

(h) tert-Butyl-[3-((E)-1-ethylbut-1-en-3-ynyl)phenoxy]-dimethylsilane 3.2 g (7.2 mmol) of tert-butyl-[3-((E)-4,4-dibromo-1-ethylbuta-1,3-dienyl)phenoxy]dimethylsilane are dissolved in 50 ml and the mixture is cooled to −78° C. 5.7 ml (14.4 mmol) of a 2.5 M solution of butyllithium are added and the medium is stirred for 2 hours, then it is treated with a saturated solution of ammonium chloride. The residue is purified by chromatography on a silica column. A yellow oil is obtained (m=1.0 g; Y=49%).

(i) 3-((E)-1-Ethylbut-1-en-3-ynyl)phenol 1 g (3.5 mmol) of tert-butyl-[3-((E)-1-ethylbut-1-en-3-ynyl)phenoxy]dimethylsilane is dissolved in 50 ml of THF, and 3.8 ml (38 mmol) of a 1.0 M solution of tetrabutylammonium fluoride are added drop by drop. The mixture is stirred for 30 minutes, then treated with a saturated solution of ammonium chloride and extracted with ethyl acetate. A yellow oil is obtained (m=690 mg; Y=100%).

(j) 2-Benzoyloxymethyl-5-[3-((E)-1-ethylbut-1-en-3-ynyl)phenoxymethyl]benzyl benzoate 610 mg (3.5 mmol) of 3-((E)-1-ethylbut-1-en-3-ynyl)phenol are dissolved in 80 ml of DMF. 150 mg (3.7 mmol) of sodium hydride are added, and the mixture is stirred at ambient temperature. 1.5 g (6.2 mmol) of 2-benzoyloxymethyl-5-bromomethylbenzyl benzoate are then added, and the medium is stirred for 2 hours. After the usual treatment and purification by chromatography on a silica gel column, a colorless oil is obtained (m=1.66 g; Y=88%).

(k) 1-(3,4-Bis-tert-butyldimethylsilyloxymethyl-benzyl-oxy)-3-((E)-1-ethylbut-1-en-3-ynyl)benzene 1.6 g (3 mmol) of 2-benzoyloxymethyl-5-[3-((E)-1-ethylbut-1-en-3-ynyl)phenoxymethyl]benzyl benzoate are dissolved in 15 ml of a 2% solution of potassium carbonate in methanol. The reaction medium is stirred for 2 hours, then treated with a saturated solution of ammonium chloride, and extracted with ethyl acetate. The residue obtained is dissolved in 20 ml of anhydrous DMF, and 900 mg (6 mmol) of tertbutyl-dimethylchlorosilane and 450 mg (6.6 mmol) of imidazole are added. The medium is stirred for 10 hours at ambient temperature. After the usual treatment, the residue obtained is purified by chromatography on a silica column (eluent heptane 85-ethyl acetate 85). An orange oil is obtained (m=1.16 g; Y=70%).

(l) (E)-6-{3-[3,4-Bis(tert-butyldimethylsilanyloxy-methyl)benzyloxy]phenyl}-1,1,1-trifluoro-2-trifluoro-methyloct-5-en-3-yn-2-ol 1.16 g (2.1 mmol) of 1-(3,4-bis-tert-butyl-dimethylsilyloxymethylbenzyloxy)-3-((E)-1-ethylbut-1-en-3-ynyl)benzene are dissolved in 30 ml of anhydrous THF, and the mixture is cooled to −78° C. 930 μl (2.3 mmol) of a 2.5 M solution of butyllithium are added drop by drop, and the medium is stirred for 15 minutes. A flow of hexafluoroacetone (gas) is passed into the solution for 10 minutes, and the reaction medium is treated with a saturated solution of ammonium chloride. The residue obtained is purified by chromatography on a silica column (eluent heptane 80-ethyl acetate 20). A yellow oil is obtained (m=1.35 g; Y=89%).

(m) (E)-6-[3-(3,4-Bis-hydroxymethylbenzyloxy) phenyl]-1,1,1-trifluoro-2-trifluoro-methyloct-5-en-3-yn-2-ol In a manner analogous to example 2i, by reaction of 350 mg (0.5 mmol) of (E)-6-{3-[3,4-bis(tert-butyldimethylsilanyloxymethyl)benzyloxy]-phenyl}1,1,1-trifluoro-2-trifluoromethyloct-5-en-3-yn-2-ol with 1.2 ml (1.2 mmol) of a 1.0 M solution of tetrabutylammonium fluoride. A colorless oil is obtained (m=210 mg; Y=80%).

$^1$H NMR (CDCl$_3$): 1.05 (t, 3H, J=7.4 Hz); 2.72 (q, 2H, J=7.4 Hz); 4.74 (s, 4H); 5.05 (s, 2H); 5.69 (s, 1H); 6.91-7.01 (m, 3H); 7.24 (m, 1H); 7.37 (s, 2H); 7.42 (s, 1H).

Example 3

(3E,5E)-6-[3-(3,4-Bis-hydroxymethylbenzyloxy) pheny]-1,1,1-trifluoro-2 trifluoromethylocta-3,5-dien-2-ol

(a) (3E,5E)-6-{3-[3,4-Bis(tert-butyldimethylsilanyloxy-methyl)benzyloxy]phenyl}-1,1,1-trifluoro-2-trifluoro-methylocta-3,5-dien-2-ol 135 mg (3.55 mmol) of lithium aluminum hydride are dissolved in 10 ml of anhydrous THF. 385 mg (7.1 mmol) of sodium methoxide are added, and the mixture is stirred at ambient temperature for 10 minutes. A solution of 860 mg (1.2 mmol) of (E)-6-{3-[3,4-bis(tertbutyldimethylsilanyloxymethyl)-benzyloxy]phenyl}-1,1,1-trifluoro-2-trifluoromethyloct-5-en-3-yn-2-ol (described in example 21) in 7 ml of THF is added drop by drop. The medium is heated to reflux for 2 hours, then treated by successive addition of 120 μl of water, 120 μl of 15% NaOH and 35 μl of water. After filtration, a thick yellowish oil is obtained (m=650 mg; Y=76%).

(b) (3E,5E)-6-[3-(3,4-Bis-hydroxymethylbenzyloxy)-phenyl]-1,1,1-trifluoro-2-trifluoromethylocta-3,5-dien-2-ol In a manner analogous to example 2m, by reaction of 640 mg (0.89 mmol) of (3E,5E)-6-{3-[3,4-bis(tert-butyldimethylsilanyloxymethyl)benzyloxy]-phenyl}1,1,1-trifluoro-2-trifluoromethylocta-3,5-dien-2-ol with 2.1 ml (2.1 mmol) of a 1.0 M solution of tetrabutylammonium fluoride. A colorless oil is obtained (m=260 mg; Y=60%).

$^1$H NMR (DMSO): 1.10 (t, 3H, J=7.5 Hz); 2.65 (q, 2H, J=7.4 Hz); 4.55 (t, 4H, J=5.2 Hz); 5.08-5.17 (m, 4H); 6.05 (d, 1H, J=15.1 Hz); 6.64 (d, 1H, J=11.2 Hz); 6.96 (dd, 1H, J1=11.2 Hz, J2=2 Hz); 7.08-7.08-7.51 (m, 6H); 8.27 (s, 1H).

Example 4

(E)-6-{3-[2-(3,4-Bis-hydroxymethylphenyl)ethyl]phenyl}-1,1,1-trifluoro-2-trifluoromethyloct-5-en-3-yn-2-ol

(a) (E)-1-(3-{2-[3,4-Bis(tert-butyldimethylsilanyloxy-methyl)phenyl]ethyl}phenyl)-4,4-dibromo-1-ethylbuta-1,3-diene In a manner analogous to example 2g, by reaction of 9 g (16.3 mmol) of (E)-3-(3-{2-[3,4-bis(tert-butyldimethylsilanyloxymethyl)-phenyl]ethyl}phenyl)pent-2-enal (prepared in example 1j) with 2.1 g (32.5 mmol) of zinc powder, 8.5 g (32.5 mmol) of triphenylphosphine and 108 g (32.5 mmol) of carbon tetrabromide. A yellow oil is obtained (m=11.3 g; Y=98%).

(b) (E)-1-(3-{2-[3,4-Bis(tert-butyldimethylsil~yloxymethyl)phenyl]ethyl}phenyl)-1-ethylbut-1-en-3-yne In a manner analogous to example 2 h, by reaction of 11.3 g (15.9 mmol) of (E)-1-(3-{2-[3,4-bis(tert-butyldimethylsilanyloxymethyl)-phenyl]ethyl}phenyl)-4,4-dibromo-1-ethylbuta-1,3-diene with 128 ml (32 mmol) of a 2.5 M solution of butyllithium. A yellow oil is obtained (m=85 g; Y=97%).

(c) (E)-6-(3-{2-[3,4-Bis(tert-butyldimethylsilanyloxy-methyl)phenyl]ethyl}phenyl)-1,1,1-trifluoro-2-tri-fluoromethyloct-5-en-3-yn-2-ol In a manner analogous to example 2l, by reaction of 5 g (9.1 mmol) of (E)-1-(3-{2-[3,4-bis(tert-butyldimethylsilanyloxymethyl)-phenyl]ethyl}phenyl)-1-ethyl-but-1-en-3-yne with 4 ml (10 mmol) of a 2.5 M solution of butyllithium and a flow of hexafluoroacetone. The desired product is obtained in the form of a yellow oil (m=3.7 g; Y=57%).

(d) (E)-6-(3-[2-(3,4-Bis-hydroxymethylphenyl)ethyl]-phenyl)-1,1,1-trifluoro-2-trifluoromethyloct-5-en-3-yn-2-ol In a manner analogous to example 2m, by reaction of 1 g (1.4 mmol) of (E)-6-(3-{2-[3,4-bis(tert-butyldimethylsilanyloxymethyl)phenyl]ethyl}-phenyl)-1,1,1-trifluoro-2-trifluoromethyloct-5-en-3-yn-2-ol with 3.3 ml (3.3 mmol) of a 1.0 M solution of tetrabutylammonium fluoride. A yellowish solid is obtained (m.p.=123° C.; m=570 mg; Y=84%).

$^1$H NMR (CDCl$_3$): 1.05 (t, 3H, J=7.5 Hz); 2.75 (q, 2H, J=7.5 Hz); 2.92 (s, 4H); 4.69 (s, 4H); 5.67 (s, 1H); 7.05-7.31 (m, 7H).

Example 5

(3E,5E)-6-{3-[2-(3,4-Bis-hydroxymethylphenyl)ethyl]-phenyl}-1,1,1-trifluoro-2-trifluoromethylocta-3,5-dien-2-ol

(a) (3E,5E)-6-(3-{2-[3,4-Bis(tert-butyldimethyl-silanyloxymethyl)phenyl]ethyl}phenyl)-1,1,1-trifluoro-2-trifluoromethylocta-3,5-dien-2-ol In a manner analogous to example 3a, by reaction of 2.5 g (3.5 mmol) of (E)-6-(3-(2-[3,4-bis(tert-butyldimethylsilanyloxymethyl)phenyl]ethyl}-phenyl)-1,1,1-trifluoro-2-trifluoromethyloct-5-en-3-yn-2-ol (described in example 4c) with 400 mg (10.4 mmol) of lithium aluminum hydride and 1.13 g (21 mmol) of sodium methoxide. A yellow oil is obtained (m=1.27 g; Y=51%).

(b) (3E,5E)-6-{3-[2-(3,4-Bis-hydroxymethylphenyl)ethyl]-phenyl}1,1,1-trifluoro-2-trifluoromethylocta-3,5-dien-2-ol In a manner analogous to example 2m, by reaction of 1.2 g (1.67 mmol) of (3E,5E)-6-(3-{2-[3,4-bis(tert-butyldimethylsilanyloxymethyl)phenyl]ethyl}phenyl)-1, 1,1-trifluoro-2-trifluoromethylocta-3,5-dien-2-ol with 4 ml (4 mmol) of a 1.0 M solution of tetrabutylammonium fluoride. A white solid is obtained (m.p.=104° C.; m=715 mg; Y=87%).

$^1$H NMR (DMSO): 1.02 (t, 3H, J=7.5 Hz); 2.66 (q, 2H, J=7.5 Hz); 2.93 (s, 4H); 4.71 (s, 2H); 4.72 (s, 2H); 5.79 (d, 1H, J=15.0 Hz); 6.24 (d, 1H, J=11.0 Hz); 7.08-7.30 (m, 8H).

Example 6

Formulation Examples

1) Oral Route (a) The following composition is prepared in the form of a 0.2 g tablet:

| | |
|---|---|
| Compound of Example 1 | 0.005 g |
| Pregelatinized starch | 0.065 g |
| Microcrystalline cellulose | 0.075 g |
| Lactose | 0.050 g |
| Magnesium stearate | 0.005 g |

For the treatment of ichthyosis, 1 to 3 tablets per day are administered to an adult individual for 1 to 12 months according to the severity of the case treated.

(b) A drinkable suspension is prepared, intended to be formulated in 5 ml ampoules:

| | | |
|---|---|---|
| Compound of example 2 | | 0.050 mg |
| Glycerol | | 0.500 g |
| 70% sorbitol | | 0.500 g |
| Sodium saccharinate | | 0.010 g |
| Methyl parahydroxybenzoate | | 0.040 g |
| Flavoring | q.s. | |
| Purified water | q.s. | 5 ml |

For the treatment of acne, 1 ampoule per day is administered to an adult individual for 1 to 12 months according to the severity of the case treated.

(c) The following formulation is prepared which is intended to be formulated in gelatine capsules:

| | | |
|---|---|---|
| Compound of example 4 | | 0.0001 mg |
| Maize starch | | 0.060 g |
| Lactose | q.s | 0.300 g |

The gelatine capsules used are formed of gelatine, of titanium oxide and of a preservative.

In the treatment of psoriasis, 1 gelatine capsule per day is administered to an adult individual for 1 to 12 months.

(d) The following formulation is prepared which is intended to be formulated in gelatine capsules:

| | | |
|---|---|---|
| Compound of example 5 | | 0.02 mg |
| Cyclosporin | | 0.050 g |
| Maize starch | | 0.060 g |
| Lactose | q.s. | 0.300 g |

The gelatine capsules used are formed of gelatine, of titanium oxide and of a preservative.

In the treatment of psoriasis, 1 gelatine capsule per day is administered to an adult individual for 1 to 12 months.

2) Topical Route (a) The following nonionic water-in-oil cream is prepared:

| | | |
|---|---|---|
| Compound of example 3 | | 0.100 g |
| Mixture of alcohols of emulsive lanolin, of waxes and of refined oils, sold by BDF under the name "Eucérine anhydre" | | 39.900 g |
| Methyl parahydroxybenzoate | | 0.075 g |
| Propyl parahydroxybenzoate | | 0.075 g |
| Sterile demineralized water | q.s | 100.000 g |

This cream is applied to a psoriatic skin 1 to 2 times per day for 1 to 12 months.

(b) A gel is prepared by producing the following formulation:

| | | |
|---|---|---|
| Compound of example 1 | | 0.001 g |
| Erythromycin base | | 4.000 g |
| Butylhydroxytoluene | | 0.050 g |
| Hydroxypropylcellulose sold by Hercules under the name of "KLUCEL HF" | | 2.000 g |
| Ethanol (to 95") | q.s | 100.000 g |

This gel is applied to a skin affected by dermatosis or an acneic skin 1 to 3 times per day for 6 to 12 weeks according to the severity of the case treated.

(c) An antiseborrheic lotion is prepared by proceeding to mix the following ingredients:

| | | |
|---|---|---|
| Compound of example 2 | | 0.030 g |
| Propylene glycol | | 5.000 g |
| Butylhydroxytoluene | | 0.100 g |
| Ethanol (to 95°) | q.s | 100.000 g |

This lotion is applied two times per day to a seborrheic scalp and a significant improvement is confirmed within a period of between 2 and 6 weeks.

(d) A cosmetic preparation against the harmful effects of the sun is prepared by proceeding to mix the following ingredients:

| | | |
|---|---|---|
| Compound of example 2 | | 1.000 g |
| Benzylidenecamphor | | 4.000 g |
| Fatty acid triglycerides | | 31.000 g |
| Glycerol monostearate | | 6.000 g |
| Stearic acid | | 2.000 g |
| Cetyl alcohol | | 1.200 g |
| Lanolin | | 4.000 g |
| Preservatives | | 0.300 g |
| Propylene glycol | | 2.000 g |
| Triethanolamine | | 0.500 g |
| Perfume | | 0.400 g |
| Demineralized water | q.s | 100.000 g |

This composition is applied daily, it allows photoinduced aging to be combated.

(e) The following nonionic Oil-in-Water cream is prepared:

| | | |
|---|---|---|
| Compound of example 3 | | 0.500 g |
| Retinoic acid | | 0.020 g |
| Cetyl alcohol | | 4.000 g |
| Glycerol monostearate | | 2.500 g |
| Propyl parahydroxybenzoate | | 0.075 g |
| PEG 50 stearate | | 2.500 g |
| Shea butter | | 9.200 g |
| Propylene glycol | | 2.000 g |
| Methyl parahydroxybenzoate | | 0.075 g |
| Sterile demineralized water | q.s | 100.000 g |

This cream is applied to a psoriatic skin 1 to 2 times per day for 30 days for attack treatment and indefinitely for maintenance.

(f) A topical gel is prepared by proceeding to mix the following ingredients:

| | | |
|---|---|---|
| Compound of example 4 | | 0.050 g |
| Ethanol | | 43.000 g |
| α-tocopherol | | 0.050 g |
| Carboxyvinyl polymer sold under the name "Carbopol 941" by "Goodrich" | | 0.500 g |
| Triethanolamine in aqueous solution at 20% by weight | | 3.800 g |
| Water | | 9.300 g |
| Propylene glycol | q.s. | 100.000 g |

This gel is applied in the treatment of acne 1 to 3 times per day for 6 to 12 weeks according to the severity of the case treated.

(g) A lotion against hair loss and for the regrowth of the hair is prepared by proceeding to mix the following ingredients:

| | |
|---|---|
| Compound of example 3 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |

| -continued | | |
|---|---|---|
| Butylhydroxyanisole | | 0.01 g |
| Butylhydroxytoluene | | 0.02 g |
| Water | q.s. | 100.00 g |

This lotion is applied 1 to 2 times per day for 3 months on a scalp which has suffered a loss of hair and indefinitely for maintenance treatment.

(h) An antiacneic cream is prepared by proceeding to mix the following ingredients:

| | | |
|---|---|---|
| Compound of example 5 | | 0.050 g |
| Retinoic acid | | 0.010 g |
| Mixture of stearates of glycerol and of polyethylene glycol (75 mol) sold under the name of "Gelot 64" by GATTEFOSSE" | | 15.000 g |
| Stone oil polyoxyethylenated with 6 mol of ethylene oxide sold under the name of "Labrafil M2 130 CS" by "GATTEFOSSE" | | 8.000 g |
| Perhydrosqualene | | 10.000 g |
| Preservatives | q.s. | |
| Polyethylene glycol (molecular mass = 400) | | 8.000 g |
| Ethylenediaminetetraacetic acid disodium salt | | 0.050 g |
| Purified water | q.s. | 100.000 g |

This cream is applied to a skin affected by dermatosis or an acneic skin 1 to 3 times per day for 6 to 12 weeks.

(i) An oil-in-water cream is prepared by producing the following formulation:

| | | |
|---|---|---|
| Compound of example 4 | | 0.020 g |
| Betamethasone 17-valerate | | 0.050 g |
| S-carboxymethylcysteine | | 3.000 g |
| Polyoxyethylene stearate (40 mol of ethylene oxide) sold under the name of "Myrj 52" by "ATLAS" | | 4.000 g |
| Sorbitan monolaurate, polyoxyethylenated with 20 mol of ethylene oxide sold under the name of "Tween 20"by "ATLAS" | | 1.800 g |
| Mixture of glyceryl mono- and distearate sold under the name of "Géléol" by "GATTEFOSSE" | | 4.200 g |
| Propylene glycol | | 10.000 g |
| Butylhydroxyanisole | | 0.010 g |
| Butylhydroxytoluene | | 0.020 g |
| Cetostearyl alcohol | | 6.200 g |
| Preservatives | q.s. | |
| Perhydrosqualene | | 18.000 g |
| Mixture of caprylic-capric triglycerides sold under the name of "Myglyol 8 12" by "DYNAMIT NOBEL" | | 4000 g |
| Triethanolamine (99% by weight) | | |
| Water | q.s. | 100.000 g |

This cream is applied 2 times per day to a skin affected by inflammatory dermatosis for 30 days.

(j) The following oil-in-water-type cream is prepared:

| | | |
|---|---|---|
| Lactic acid | | 5.000 g |
| Compound of example 1 | | 0.020 g |
| Polyoxyethylene stearate (40 mol of ethylene oxide) sold under the name "Myrj 52" by the company "ATLAS" | | 4.000 g |

| -continued | | |
|---|---|---|
| Sorbitan monolaurate, polyoxyethylenated with 20 mol of ethylene oxide sold under the name of "Tween 20" by the company "ATLAS" | | 1.800 g |
| Mixture of glyceryl mono- and distearate sold under the name "Geleol" by the company "GATTEFOSSE" | | 4.200 g |
| Propylene glycol | | 10.000 g |
| Butylhydroxyanisole | | 0.010 g |
| Butylhydroxytoluene | | 0.020 g |
| Cetostearyl alcohol | | 6.200 g |
| Preservatives | q.s. | |
| Perhydrosqualene | | 18.000 g |
| Mixture of caprylic-capric triglycerides sold under the name of "Miglyol 8 12" by the company "DYNAMIT NOBEL" | | 4.000 g |
| Water | q.s | 100.000 g |

This cream is applied once per day, it helps combat aging, whether photoinduced or chronological.

(k) The following anhydrous salve is prepared:

| | | |
|---|---|---|
| Compound of example 1 | | 5.000 g |
| Liquid petroleum jelly | | 50.00 g |
| Butylhydrotoluene | | 0.050 g |
| White petroleum jelly | q.s | 100 g |

This salve is applied twice per day to a skin affected by squamous dermatosis for 30 days.

3) Intralesional Route (a) The following composition is prepared:

| | | |
|---|---|---|
| Compound of example 2 | | 0.002 g |
| Ethyl oleate | q.s. | 10 g |

In the treatment of malignant melanoma, the composition is injected into an adult individual at a rate of 1 to 7 times per week for 1 to 12 months.

(b) The following composition is prepared:

| | | |
|---|---|---|
| Compound of example 1 | | 0.050 g |
| Olive oil | q.s. | 2 g |

In the treatment of basocellular carcinoma, the composition is injected into an adult individual at a rate of 1 to 7 times per week for 1 to 12 months.

(c) The following composition is prepared:

| | | |
|---|---|---|
| Compound of example 3 | | 0.1 mg |
| Sesame oil | q.s. | 2 g |

In the treatment of spinocellular carcinoma, the composition is injected into an adult individual at a rate of 1 to 7 times per week for 1 to 12 months.

(d) The following composition is prepared:

| | | |
|---|---|---|
| Compound of example 4 | | 0.001 mg |
| Methyl benzoate | q.s. | 10 g |

In the treatment of carcinoma of the colon, the composition is injected into an adult individual at a rate of 1 to 7 times per week for 1 to 12 months.

4) Intravenous Route:

(a) The following injectable lipid emulsion is prepared:

| | | |
|---|---|---|
| Compound of example 4 | | 0.001 mg |
| Soya oil | | 10.000 g |
| Egg phospholipid | | 1.200 g |
| Glycerol | | 2.500 g |
| Water for injectable | q.s.p. | 100.000 g |

In the treatment of psoriasis, the composition is injected into an adult individual at a rate of 1 to 7 times per week for 1 to 12 months.

(b) The following injectable lipid emulsion is prepared:

| | | |
|---|---|---|
| Compound of example 1 | | 0.010 g |
| Cotton oil | | 10.000 g |
| Soya lecithin | | 0.750 g |
| Sorbitol | | 5.000 g |
| DL, α tocopherol | | 0.100 g |
| Water for injectable | q.s.p. | 100.000 g |

In the treatment of ichthyosis, the composition is injected into an adult individual at a rate of 1 to 7 times per week for 1 to 12 months.

(c) The following injectable lipid emulsion is prepared:

| | | |
|---|---|---|
| Compound of example 2 | | 0.001 g |
| Soya oil | | 15.000 g |
| Acetylated monoglycerides | | 10.000 g |
| Pluronic F-108 | | 1.000 g |
| Glycerol | | 2.500 g |
| Water for injectable | q.s.p | 100.000 g |

In the treatment of leukemia, the composition is injected into an adult individual at a rate of 1 to 7 times per week for 1 to 12 months.

(d) The following mixed micelle composition is prepared:

| | | |
|---|---|---|
| Compound of example 2 | | 0.001 g |
| Lecithin | | 16.930 g |
| Glycocholic acid | | 8.850 g |
| Water for injectable | q.s.p. | 100.000 g |

In the treatment of malignant melanoma, the composition is injected into an adult individual at a rate of 1 to 7 times per week for 1 to 12 months.

(e) The following cyclodextrin composition is prepared:

| | | |
|---|---|---|
| Composition of example 3 | | 0.1 mg |
| beta-cyclodextrin | | 0.100 g |
| Water for injectable | q.s.p. | 10.000 g |

In the treatment of transplant rejection, the composition is injected into an adult individual at a rate of 1 to 7 times per week for 1 to 12 months.

(f) The following cyclodextrin composition is prepared:

| | | |
|---|---|---|
| Compound of example | | 0.010 g |
| 2-hydroxypropylcyclodextrin | | 0.100 g |
| Water for injectable | q.s.p | 10.000 g |

In the treatment of cancer of the kidney, the composition is injected into an adult individual at a rate of 1 to 7 times per week for 1 to 12 months.

Example 7

Example of Evaluation Test of the Biological Activity of the Compounds of the Invention Transactivation Potential The VDR agonist activity can be tested on the HeLa cell line, by cotransfection of an expression vector of the human VDR receptor and of the p240Hase-CAT reporter plasmid which contains the region −1399 to +76 of the rat 24-hydroxylase promoter, cloned upstream of the phase coding for the chloramphenicol acetyltransferase (CAT) gene. 18 hours after cotransfection, the test product is added to the medium. After treatment for 18 hours, the measurement of the CAT activity of the cell lysates is carried out by means of an Elisa test (Enzyme Linked Immuno Sorbent Essay, test marketed by Roche Molecular Biochemicals). The agonist activity can be characterized in this cotransfection system by the determination of the dose necessary in order to obtain 50% of the maximum activity of the product (AC50).

TABLE 1

| COMPOUND | AC50 nM |
|---|---|
| Example 1 | 39 |
| Example 59 of D1 | 124 |
| Example 2 | 77 |
| Example 80 of D1 | 746 |
| Example 3 | 7 |
| Example 92 of D1 | 79 |
| Example 4 | 16 |
| Example 80 of D1 | 746 |
| Example 5 | 3 |
| Example 60 of D1 | 319 |

Figure 5:
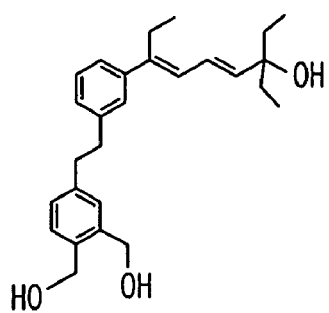
FIG. 5 is a diagram showing the chemical structures of the compounds of Examples 1, 2 and 3 and of Examples 59, 80 and 92 of WO 00/26167 (reference D1).
Figure 5:
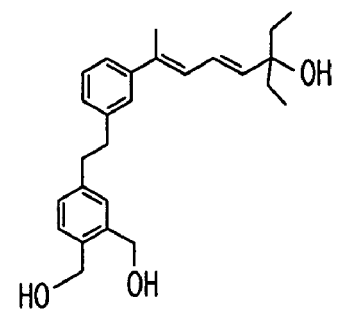
Figure 5:
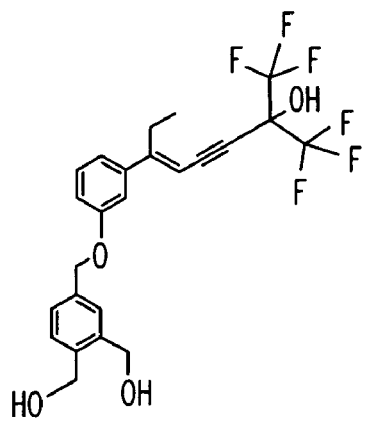
Figure 5:
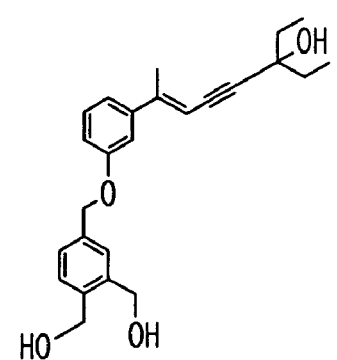
Figure 5:
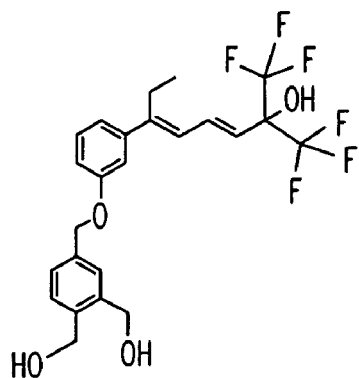
Figure 5:
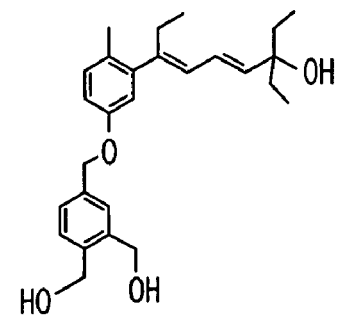
Figure 6:
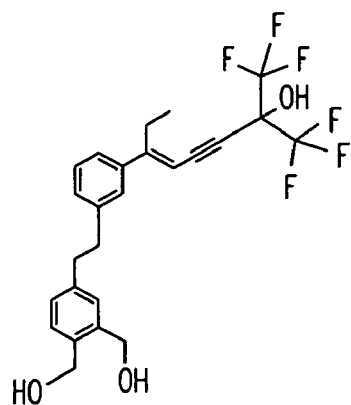
FIG. 6 is a diagram showing the chemical structures of the compounds of Examples 4 and 5 and of Examples 80 and 60 of WO 00/26167 (reference D1).
Figure 6:
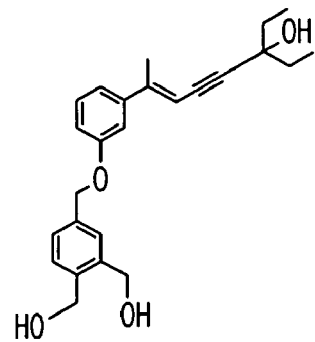
Figure 6:
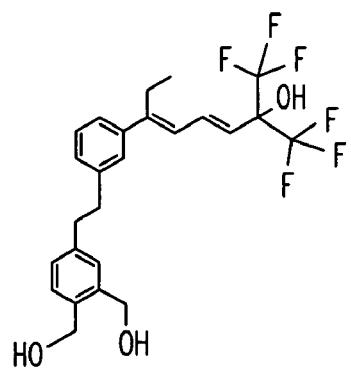
Figure 6:
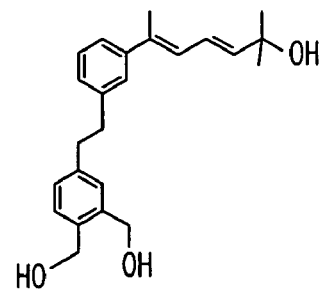

Each compound according to the invention has been compared to the structurally closest compound protected in WO 00/26167 (D1). To facilitate the comparison, the structures of the compounds of the invention and of the comparative examples of D1 are assembled in the FIGS. 5 and 6. The results show the significantly stronger activity of the compounds of the invention with respect to the compounds of D1. A difference between two values of AC50 is considered as significant if it is at least a factor of 3, preferentially a factor of 5 and more preferentially a factor of 10.

Example 8

Example of Evaluation Test of the Biological Activity of the Compounds of the Invention Activity on the Proliferation of Human Keratinocytes It is known that 1,25-dihydroxyvitamin D3, called calcitriol and corresponding to natural vitamin D, inhibits the proliferation of human keratinocytes in culture. The method used is the following: the normal human keratinocytes are inoculated at low density into a 24-well plate. After 4 hours, the compounds to be tested are added to the culture medium. After culturing for 5 days, the proliferation of the keratinocytes is determined by incorporation of 5-bromo-2' deoxyuridine (BrdU) in the DNA. The quantity of BrdU incorporated is then quantified by using the Elisa test (Enzyme Linked Immuno Sorbent Essay, test marketed by Roche Molecular Biochemicals).

The inhibitory effect on the proliferation of the keratinocytes of the compounds according to the invention and of the calcitriol used as a reference compound is summarized in table II which follows. The Ic 50 value indicates the concentration of compound tested for which the compound inhibits the proliferation of the keratinocytes by 50%.

These results allow an inhibitory activity on the proliferation of the keratinocytes to be demonstrated for the compounds according to the invention in the same ranges of value as that of calcitriol (natural vitamin D). In addition, the results show significant differences between the compounds according to the invention and the structurally closest compounds of D1. A difference is considered as significant between two values of AC50 if it is at least a factor of 3, preferentially a factor of 5 and more preferentially a factor of 10.

TABLE II

| COMPOUND | INHIBITION OF PROLIFERATION IC50* (nM) |
| --- | --- |
| Calcitriol | 14 |
| Example 1 | 45 |
| Example 80 of D1 | 1029 |
| Example 2 | 153 |
| Example 80 of D1 | >10,000 (nonactive) |
| Example 3 | 35 |
| Example 92 of D1 | 99 |
| Example 4 | 29 |
| Example 80 of D1 | >10,000 (nonactive) |
| Example 5 | 8 |
| Example 60 of D1 | 1506 |

*Concentration for which a 50% inhibition of the proliferation of the keratinocytes is obtained.

Example 9

Example of Evaluation Test of the Biological Activity of the Compounds of the Invention Activity on the Differentiation of HL60 Cells Calcitriol induces the differentiation of promyelocytic leukemia cells (HL60) in monocytes/macrophages. This differentiation inductor effect is a well-characterized marker of cellular vitamin D activity. One of the most important antimicrobial products of macrophages is hydrogen peroxide, which can be analyzed experimentally by the reduction of NBT (Nitroblue Tetrazolium).

The method used is the following: The HL60 cells are inoculated into 6-well plates and then treated immediately with the compounds to be tested. After 4 days in culture, the cells are incubated with phorbol TPA ester and NBT for a short period and the differentiated cells, i.e., positive to NBT, are counted.

The inductor effect of the differentiation on the HL60 cells, compounds according to the invention as well as that of the reference compound calcitriol is clarified in table III below.

TABLE III

| Compound | Activation of Differentiation |
| --- | --- |
|  | AC 50? (nM) |
| Calcitriol | 7 |
|  | (n = 5) |
| Example 1 | 56 |
|  | (n = 3) |
| Example 59 of D1 | 310 |
| Example 3 | 7 |
|  | (n = 2) |
| Example 5 | 5 |
|  | (n = 2) |

* Concentration for which 50% of the maximum response of activation of differentiation is obtained.

These results show that examples 3 and according to the invention have an induction of differentiation activity on HL60 cells similar to that of calcitriol.

Example 10

Example of Evaluation Test of the Biological Activity of the Compounds of the Invention "In vivo" Induction of 24-hydroxylase in SKH Mice 24-Hydroxylase is a cytochrome P450 enzyme which hydroxylates 1,25-dihydroxyvitamin D3 (calcitriol) in position 24 resulting in a metabolite 24,25-trihydroxy-vitamin D3. It has been shown by Voorhees and al. (JID 1997, 108: 513-518) that the expression of the 24-hydroxylase gene was induced by calcitriol in human skin.

Consequently, the agonist activity on receptors of vitamin D of the compounds of the invention can be evaluated "in vivo" by induction of 24-hydroxylase in SKH mice.

The method used is the following: XII mice receive a single topical application of a compound to be tested in solution in ethanol at increasing concentrations. A volume of 50 µl of the product to be tested or of the vehicle alone is applied on the back of the mice with the aid of a pipette.

Other SKH mice receive a single topical application of calcitriol in solution in ethanol at increasing concentrations. A volume of 50 µl of the product to be tested or of the vehicle alone is applied on the back of the mice with the aid of a pipette.

8 hours after topical application, the mice are euthanized, the treated skin is removed and the epidermidis is separated from the dermis. The quantification of the MRNA of the 24-Hydroxylase is carried out by semiquantitative PCR. The results are standardized with respect to the expression of the mRNA of GAPDH and the values for the different concentrations of calcitriol tested and, for the different compounds of the invention tested, are expressed as an induction factor with respect to calcitriol.

The results are summarized in table IV which follows:

TABLE IV

MRNA EXPRESSION OF 24-HYDROXYLASE

| Compound Tested | Concentration % (weight/volume) | Induction Factor Versus Ethanol |
|---|---|---|
| Calcitriol | 0.0001 | 6.7 |
| Calcitriol | 0.001 | 10.3 |
| Calcitriol | 0.01 | 20.1 |
| Calcitriol | 0.1 | 26 |

These results show that calcitriol administered by single topical application induces the expression of the mRNA of 24-hydroxylase in the epidermidis in a dose-dependent manner in mice.

The biological activity of the compounds of the invention is evaluated by comparison between the induction factors obtained for the compounds of the invention and the induction factors obtained for calcitriol. The results are presented in table V which follows:

TABLE V

| Compound Tested | Concentration % (weight/volume) | Induction in % vs Induction Calcitriol Tested at 0.01% |
|---|---|---|
| Calcitriol | 0.01 | 100 |
| Example 1 | 0.1 | 108 |
| Example 2 | 0.01 | 58 |
| Example 3 | 0.001 | 59 |
| Example 4 | 0.01 | 89 |
| Example 5 | 0.0003 | 106 |

Thus, these results show that the examples according to the invention have an activity comparable or very superior (examples 3 and 5) to that of calcitriol.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound selected from the group consisting of:

(E)-6-[3-(3,4-bis-hydroxymethylbenzyloxy)phenyl]-1,1,1-trifluoro-2-trifluoromethyloct-5-en-3-yn-2-ol,

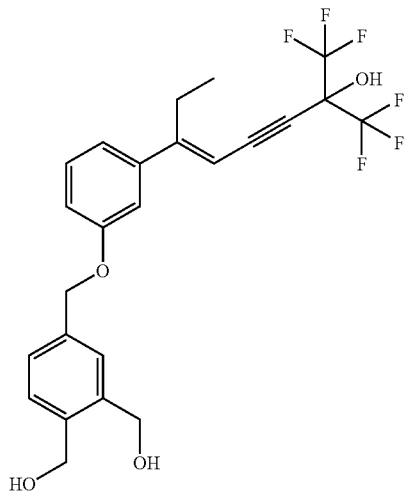

(3E,5E)-6-[3-(3,4-bis-hydroxymethylbenzyloxy)-phenyl]-1,1,1-trifluoro-2-trifluoromethylocta-3,5-dien-2-ol,

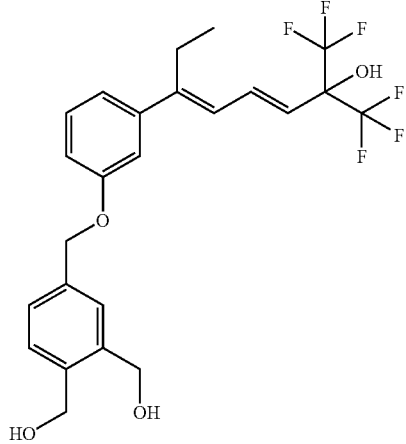

(E)-6-{3-[2-(3,4-bis-hydroxymethylphenyl)ethyl]-phenyl)-1,1,1-trifluoro-2-trifluoromethyloct-5-en-3-yn-2-ol,

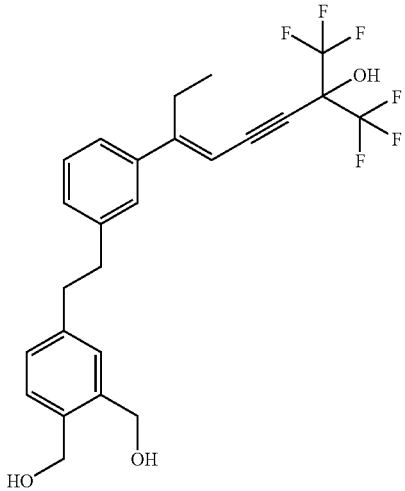

and
(3E,5E)-6-{3-[2-(3,4-bis-hydroxymethylphenyl)-ethyl]phenyl)-1,1,1-trifluoro-2-trifluoromethylocta-3,5-dien-2-ol,

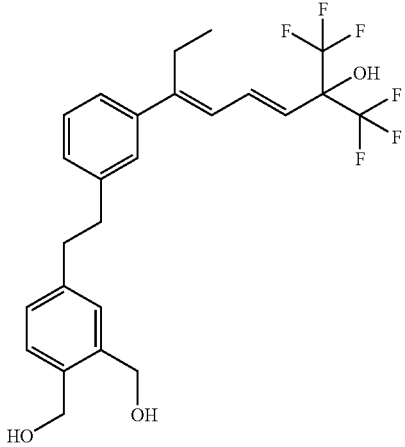

the geometric isomers thereof and these compounds in which one or more of the hydroxyl functions are protected by a protective group —(C=O)—R, in which R is a linear or branched alkyl radical having from 1 to 6 carbon atoms, an aryl radical having from 6 to 10 carbon atoms, or an aralkyl radical having from 7 to 11 carbon atoms, the aryl radical or the aralkyl radical optionally being mono- or disubstituted by a hydroxy group, an alkoxy radical having from 1 to 3 carbon atoms, a halogen atom, a nitro function or by an amino function, and mixtures thereof.

2. The compound as defined by claim 1, comprising at least one protective group —(C=O)—R, in which R is a methyl, ethyl, isopropyl, tert-butyl or hexyl radical.

3. The compound as defined by claim 1, comprising at least one protective group —(C=O)—R, in which R is a phenyl or naphthyl radical.

4. The compound as defined by claim 1, comprising at least one protective group —(C=O)—R, in which R is a benzyl or methylnaphthyl radical.

5. The compound as defined by claim 1, comprising at least one protective group —(C=Q)-R, in which R is a fluorine, bromine or chlorine atom.

6. A pharmaceutical composition comprising an effective cell proliferation and differentiation affecting amount of at least one compound as defined by claim 1.

7. The pharmaceutical composition as defined by claim 6, further comprising at least one of a retinoid, a corticosteroid, an estrogen, an antioxidant, an α-hydroxy acid, a β-hydroxy acid, an α-keto acid or a salt, an amide or an ester thereof, an ion channel blocker, an immune system affecting active agent, or a mixture thereof.

8. The pharmaceutical composition as defined by claim 6, said at least one compound comprising from 0.0001% to 5% by weight thereof.

9. The pharmaceutical composition as defined by claim 6, formulated as tablets, capsules, a syrup, a suspension, a powder, granules, an emulsion, micropheres, nanospheres, controlled release lipid vesicles or polymers, a solution, a salve, a cream, a milk, an ointment, a lotion, a gel, a spray, or a swab.

10. A pharmaceutical composition comprising the compound of claim 1 and at least one member selected from the group consisting of 2-hydroxypropylcyclodextrin, acetylated monoglycerides, beta-cyclodextrin butylhydrotoluene, butylhydroxyanisole, butylhydroxytoluene, carboxyvinyl polymer, cetostearyl alcohol, cetyl alcohol, cotton oil, egg phospholipid, ethanol, ethyl oleate, ethylenediaminetetraacetic acid disodium salt, glycerol, glycerol monostearate, glycocholic acid, hydroxypropylcellulose, lactic acid, lactose, lanolin, lecithin, liquid petroleum jelly, magnesium stearate, maize starch, methyl benzoate, methyl parahydroxybenzoate, microcrystalline cellulose, mixture of caprylic-capric triglycerides, mixture of glyceryl mono- and distearate, mixture of stearates of glycerol and polyethylene glycol, olive oil, PEG 50 stearate, perhydrosqualene, Pluronic F-108, polyethylene glycol, polyoxyethylene stearate, pregelatinized starch, preservative, propyl parahydroxybenzoate, propylene glycol, sesame oil, shea butter, sodium saccharinate, sorbitan monolaurate polyoxyethylenated with ethylene oxide, sorbitol, soya lecithin, soya oil, stone oil polyoxyethylenated with ethylene oxide, triethanolamine, water and white petroleum jelly.

* * * * *